(12) United States Patent
Billodeaux et al.

(10) Patent No.: US 9,388,105 B2
(45) Date of Patent: Jul. 12, 2016

(54) PRODUCTION OF HYDROXY ETHER HYDROCARBONS BY LIQUID PHASE HYDROGENOLYSIS OF CYCLIC ACETALS OR CYCLIC KETALS

(75) Inventors: Damon Ray Billodeaux, Longview, TX (US); Thomas James Devon, Longview, TX (US); Jonathan Michael Penney, Gray, TN (US); Daniel Latham Terrill, Bristol, TN (US); Robert Thomas Hembre, Johnson City, TN (US); Jerome Leonard Stavinoha, Jr., Longview, TX (US)

(73) Assignee: Eastman Chemical Company, Kingsport, TN (US)

( * ) Notice: Subject to any disclaimer, the term of this patent is extended or adjusted under 35 U.S.C. 154(b) by 523 days.

(21) Appl. No.: 13/168,304

(22) Filed: Jun. 24, 2011

(65) Prior Publication Data

US 2012/0330069 A1     Dec. 27, 2012

(51) Int. Cl.
    *C07C 41/28*     (2006.01)
(52) U.S. Cl.
    CPC .................................. *C07C 41/28* (2013.01)
(58) Field of Classification Search
    USPC ................................................. 568/678, 680
    See application file for complete search history.

(56) References Cited

U.S. PATENT DOCUMENTS

| | | |
|---|---|---|
| 2,425,042 A | 8/1947 | McNamee et al. |
| 2,429,878 A | 10/1947 | Gresham et al. |
| 2,486,024 A | 10/1949 | Hearne et al. |
| 3,275,680 A | 9/1966 | Holzrichter et al. |
| 4,024,159 A | 5/1977 | Peterson |
| 4,038,175 A | 7/1977 | Bhasin |
| 4,062,898 A | 12/1977 | Dubeck et al. |
| 4,071,568 A | 1/1978 | Onoda et al. |
| 4,088,700 A | 5/1978 | Watts |
| 4,169,959 A | 10/1979 | Arpe |
| 4,308,403 A | 12/1981 | Knifton |
| 4,317,943 A | 3/1982 | Knifton |
| 4,356,327 A | 10/1982 | Knifton |
| 4,357,477 A | 11/1982 | Knifton |
| 4,375,394 A | 3/1983 | Devon |
| 4,390,734 A | 6/1983 | Knifton |
| 4,430,253 A | 2/1984 | Dubeck |
| 4,435,595 A | 3/1984 | Agreda et al. |
| 4,478,017 A | 10/1984 | Brown et al. |
| 4,479,017 A | 10/1984 | Ayusawa et al. |
| 4,482,753 A | 11/1984 | Tai-Huang et al. |
| 4,484,009 A | 11/1984 | Ghenassia et al. |
| 4,537,980 A | 8/1985 | Greenshields |
| 4,568,780 A | 2/1986 | Knifton |
| 4,617,287 A | 10/1986 | Lyons |
| 4,618,729 A | 10/1986 | Duggan et al. |
| 4,663,489 A | 5/1987 | Duggan et al. |
| 4,692,426 A | 9/1987 | Duggan et al. |
| 4,847,425 A | 7/1989 | Degner et al. |
| 4,895,818 A | 1/1990 | Duggan et al. |
| 4,895,987 A | 1/1990 | Duggan et al. |
| 4,939,294 A | 7/1990 | Agreda et al. |
| 5,319,148 A | 6/1994 | Karcher et al. |
| 5,362,918 A | 11/1994 | Aizawa et al. |
| 5,399,631 A | 3/1995 | Egawa et al. |
| 5,446,208 A | 8/1995 | Koshino et al. |
| 5,446,210 A | 8/1995 | Hees et al. |
| 5,523,491 A | 6/1996 | Egawa et al. |
| 5,589,597 A | 12/1996 | Egawa et al. |
| 5,616,736 A | 4/1997 | Thigpen |
| 5,720,895 A * | 2/1998 | Nakagawa et al. ............. 252/68 |
| 5,763,691 A | 6/1998 | Kawabe |
| 5,780,687 A | 7/1998 | Holderich et al. |
| 5,821,391 A | 10/1998 | Holderich et al. |
| 5,866,735 A | 2/1999 | Cheung |
| 5,886,198 A | 3/1999 | Ogawa et al. |
| 5,917,059 A | 6/1999 | Bruchmann et al. |
| 5,935,896 A | 8/1999 | Dupuis et al. |
| 6,013,844 A | 1/2000 | Heineke et al. |
| 6,015,875 A | 1/2000 | Smith et al. |
| 6,028,215 A | 2/2000 | Bessling et al. |
| 6,080,897 A | 6/2000 | Kawabe |
| 6,087,539 A | 7/2000 | Yamasaki et al. |
| 6,124,479 A | 9/2000 | Hinoue et al. |
| 6,136,576 A | 10/2000 | Diaz-Torres |
| 6,143,908 A | 11/2000 | Hinoue et al. |
| 6,166,240 A | 12/2000 | Jiang et al. |

(Continued)

FOREIGN PATENT DOCUMENTS

| | | |
|---|---|---|
| CA | 1 254 190 | 5/1989 |
| DE | 419223 C | 9/1925 |

(Continued)

OTHER PUBLICATIONS

Knifton "Syngas reactions: Part VIII: The preparation of glycol monoalkyl ethers," Journal of Molecular Catalysis 1985, 30, pp. 281-297.

Jakab et al. "Synthesis, regioselective hydrogenolysis, partial hydrogenation, and conformational study of dioxane and dkoxane-type (9-anthracenyl)methylene acetals of sugars," Carbohydrate Research 2009, 344, pp. 2444-2453.

Broekhuis et al. "Recovery of Propylene Glycol from Dilute Aqueous Solutions via Reversible Reaction with Aldehydes" Ind. Eng. Chem. Res. 1994, 33, pp. 3230-3237.

Dhale et al. "Propylene Glycol and Ethylene Glycol Recovery from Aqueous Solution via Reactive Distillation" Chemical Engineering Science, 2004, 59, pp. 2881-2890.

(Continued)

*Primary Examiner* — Rosalynd Keys
(74) *Attorney, Agent, or Firm* — Phan Law Group PLLC

(57) ABSTRACT

A liquid phase hydrogenolysis of acetal compounds, such as cyclic acetals and cyclic ketals, is disclosed. The acetal compounds are fed to a reaction zone and reacted in the presence of a noble metal catalyst supported on a carbon or silica support to make hydroxy mono-ether compounds in high selectivity, without the necessity of using acidic co-catalysts such as phosphorus containing acids or stabilizers such as hydroquinone.

25 Claims, No Drawings

(56) References Cited

U.S. PATENT DOCUMENTS

| | | | |
|---|---|---|---|
| 6,207,850 B1 | 3/2001 | Jiang et al. |
| 6,232,512 B1 | 5/2001 | Haas et al. |
| 6,265,623 B1 | 7/2001 | Morawietz et al. |
| 6,291,725 B1 | 9/2001 | Chopade |
| 6,380,419 B2 | 4/2002 | Kawabe |
| 6,458,992 B1 | 10/2002 | Lederer et al. |
| 6,518,464 B2 | 2/2003 | Therre et al. |
| 6,548,681 B1 | 4/2003 | Chopade et al. |
| 6,657,089 B1 | 12/2003 | Nagasawa et al. |
| 6,670,489 B2 | 12/2003 | Koyama et al. |
| 6,713,640 B2 | 3/2004 | Miller et al. |
| 6,969,779 B2 | 11/2005 | Brewer et al. |
| 7,030,277 B2 | 4/2006 | Groten et al. |
| 7,060,372 B2 | 6/2006 | Fryd et al. |
| 7,071,362 B2 | 7/2006 | Sugawara et al. |
| 7,160,524 B2 | 1/2007 | Lederer et al. |
| 7,301,055 B2 | 11/2007 | Hoffmockel et al. |
| 7,488,851 B2 | 2/2009 | Egidio Rodrigues et al. |
| 7,498,451 B2 | 3/2009 | Haderlein et al. |
| 7,534,922 B2 | 5/2009 | Gorling et al. |
| 7,754,900 B2 | 7/2010 | Siegert et al. |
| 9,056,313 B2 | 6/2015 | Devon et al. |
| 2003/0187281 A1* | 10/2003 | Miller et al. ............... 549/430 |
| 2006/0129000 A1 | 6/2006 | Goring et al. |
| 2008/0283384 A1 | 11/2008 | Lang et al. |
| 2010/0048940 A1 | 2/2010 | Tulchinsky et al. |
| 2010/0099894 A1 | 4/2010 | Dubois et al. |
| 2010/0158780 A1 | 6/2010 | Galligan et al. |
| 2010/0228065 A1 | 9/2010 | Cheung et al. |
| 2010/0261936 A1 | 10/2010 | Okumura et al. |
| 2010/0292491 A1 | 11/2010 | Selifonov et al. |
| 2011/0034739 A1 | 2/2011 | Stochniol et al. |
| 2011/0207969 A1 | 8/2011 | Olken et al. |
| 2012/0121911 A1 | 5/2012 | Mullen et al. |

FOREIGN PATENT DOCUMENTS

| | | | |
|---|---|---|---|
| DE | 3328561 A1 | 2/1985 |
| DE | 238 232 A1 | 8/1986 |
| DE | 238232 A1 | 8/1986 |
| DE | 19648960 A1 | 5/1998 |
| DE | 10036423 A1 | 3/2001 |
| EP | 0 168 989 A1 | 1/1986 |
| EP | 0 169 666 B1 | 1/1986 |
| EP | 0271091 A1 | 6/1988 |
| EP | 0 312 659 A1 | 4/1989 |
| EP | 0499055 A2 | 8/1992 |
| EP | 0616994 A2 | 9/1994 |
| EP | 0 624 563 A1 | 11/1994 |
| EP | 0696564 A1 | 2/1996 |
| EP | 1236511 A1 | 9/2002 |
| FR | 2906246 A | 3/2008 |
| GB | 1020500 A | 2/1966 |
| GB | 1046608 * | 10/1966 |
| JP | 52073810 A | 6/1977 |
| JP | 56166186 A | 12/1981 |
| JP | 58198431 A | 11/1983 |
| JP | 5155878 A | 6/1993 |
| JP | 5271217 A | 10/1993 |
| JP | 6128184 A | 5/1994 |
| JP | 7-224055 A | 8/1995 |
| JP | 2001031671 A * | 2/2001 |
| JP | 2001072636 A | 3/2001 |
| JP | 4287546 B2 | 7/2009 |
| WO | WO 01/19763 A1 | 3/2001 |
| WO | WO 03/002547 A1 | 1/2003 |
| WO | WO 2010/027663 A1 | 3/2010 |

OTHER PUBLICATIONS

Hao et al. "Downstream processing of 1,3-propanediol fermentation broth" J. Chem. Technol. Biotechnol. 2006, 81, pp. 102-108.
Howard et al. "Hydrogenolysis of Ketals" J. Org. Chem., 1961 26(4), pp. 1026-1028.
Osman et al. "Cyclic Acetal Formation Between 2-Pyridinecarboxaldehyde and y-Hydroxy-a,b-Acetylenic Esters" Tetrahedron Lett. 2008, 49 (46) pp. 6550-6552.
Zajac et al. "Reaction of 2-Butynal Diethyl Acetal with Lithium Aluminum Hydride" J. Org. Chem., 1975 40(4), pp. 530-531.
Astle et al. "Catalysis with Cation-Exchange Resins, Preparation of 1,3 Dioxolanes and 1,3,6-Trioxocanes", Industrial and Engineering Chemistry, Apr. 1954, pp. 787-791.
Singh et al. "Production of Butyl Acetate by Catalytic Distillation. Theoretical and Experimental Studies" Ind. Eng. Chem. Res. 2005, 44, pp. 3042-3052.
Venimadhavan et al. "A Novel Distillate Policy for Batch Reactive Distillation with Application to the Production of Butyl Acetate" Ind. Eng. Chem. Res. 1999, 38, pp. 714-722.
Chadda et al. "Feasibility and Synthesis of Hybrid Reactive Distillation Systems" AIChE Journal, Dec. 2002, vol. 48, No. 12, pp. 2754-2768.
Hibbert et al., J. Am. Chem. Soc. 1924, 46(5), pp. 1283-1290.
Sulzbacher et al., J. Am. Chem. Soc. 1948, 70(8), pp. 2827-2828.
Bronsted and Grove, J. Am. Chem. Soc. 1930, 52(4), pp. 1394-1403.
Van Duzee et al., J. Am. Chem. Soc. 1935, 57, p. 147.
Bonner et al., J. Am. Chem. Soc., Perkins Trans. 1981, pp. 1807-1810.
Tkachenko et al. "Research in the Field of Furan Acetal Compounds. XII. Features of the Vapor-Phase Hydrogenation of Disubstituted 1,3-Dioxolanes", Chemistry and Technology of Furan Compounds, 1985, pp. 59-64.
Public Dow literature, "Dow Technology Licensing—METEOR™ Ethylene Oxide/Glycol Process Technology," http://www.dow.com/licensing/offer/meteor.htm (downloaded and printed from the internet on Aug. 24, 2011).
Public Shell literature, "Factsheets: OMEGA and ethylene oxide/ethylene glycol technology," http://www.shell.com/home/content/chemicals/aboutshell/media_centre/factsheets/omega/ (downloaded and printed from the internet on Aug. 24, 2011).
Public website at http://globalbiochemna.com/, Global BioChem Technology Group (GBT), Product Information, "About Us, and Glycols Project/Polyol Chemicals" (downloaded and printed from the internet on Aug. 24, 2011).
Public Dow literature, Dow Product Safety Assessment, "Ethylene Glycol Butyl Ether" (EGBE), at http://www.dow.com/productsafety, Product Safety Assessment Finder. (downloaded and printed from the internet on Aug. 24, 2011).
Kul'nevich et al., Khimiya Geterotsiklicheskikh Soyedinenii, No. 8, 1977, pp. 1026-1029.
U.S. Appl. No. 13/168,229, filed Jun. 24, 2011.
U.S. Appl. No. 13/168,274, filed Jun. 24, 2011.
U.S. Appl. No. 13/168,330, filed Jun. 24, 2011.
U.S. Appl. No. 13/168,349, filed Jun. 24, 2011.
U.S. Appl. No. 13/168,361, filed Jun. 24, 2011.
U.S. Appl. No. 13/168,374, filed Jun. 24, 2011.
Coelho, Antonio Carlos Vieira, et al.; "Surface Area, Crystal Morphology and Characterization of Transition Alumina Powders from a New Gibbsite Precursor"; Materials Research, vol. 10, No. 2, pp. 183-189 , 2007.
Hudson, L. Keith, et al.; "Aluminum Oxide", Internet Citation XP-002596245, pp. 1-40, Jun. 15, 2000, URL: http://onlinelibrary.wiley.com/doi/10.
Luyben, William L., et al.; "Reactive Distillation Design and Control", John Wiley & Sons, 2008, p. 514-517.
Hibbert, H., et al.: Studies on the reactions relating to carbohydrates and polysaccharides. X. Synthesis and relative stability of cyclic acetals from 1, 2- and 1, 3-glycols; Journal of the American Chemistry Society, vol. 46, No. 5, 1924. pp. 1283-1290, XP002621973, cited in the application pp. 1286, 1287, "Experimental Part".
Stichlmair, Johann, et al.; "Reactive Distillation Processes"; Chemical Engineering Technology, 22 (1999) 2; pp. 95-103.
Notification of Transmittal of the International Search Report and the Written Opinion of the International Searching Authority dated Jun. 19, 2012 for International Application No. PCT/US2012/043085.
Notification of Transmittal of the International Search Report and the Written Opinion of the International Searching Authority dated Jun. 14, 2012 for International Application No. PCT/US2012/042378.

(56) References Cited

OTHER PUBLICATIONS

Notification of Transmittal of the International Search Report and the Written Opinion of the International Searching Authority dated Jun. 8, 2012 for International Application No. PCT/US2012/041459.
Notification of Transmittal of the International Search Report and the Written Opinion of the International Searching Authority dated Sep. 3, 2012 for International Application No. PCT/US2012/042458.
Notification of Transmittal of the International Search Report and the Written Opinion of the International Searching Authority dated Sep. 11, 2012 for International Application No. PCT/US2012/043071.
Notification of Transmittal of the International Search Report and the Written Opinion of the International Searching Authority dated Oct. 15, 2012 for International Application No. PCT/US2012/042453.
Notification of Transmittal of the International Search Report and the Written Opinion of the International Searching Authority dated Sep. 14, 2012 for International Application No. PCT/US2012/043093.
USPTO Office Action dated Nov. 9, 2012 for co-pending U.S. Appl. No. 13/168,374.
USPTO Office Action dated Nov. 26, 2012 for co-pending U.S. Appl. No. 13/168,229.
USPTO Office Action dated May 21, 2013 for co-pending U.S. Appl. No. 13/168,374.
USPTO Office Action dated Jul. 1, 2013 for co-pending U.S. Appl. No. 13/168,229.
USPTO Office Action dated Aug. 15, 2013 for co-pending U.S. Appl. No. 13/168,330.
USPTO Office Action dated Nov. 1, 2013 for co-pending U.S. Appl. No. 13/168,274.
USPTO Office Action dated Nov. 1, 2013 for co-pending U.S. Appl. No. 13/168,349.
USPTO Office Action dated Nov. 4, 2013 for co-pending U.S. Appl. No. 13/168,361.
USPTO Office Action dated Feb. 26, 2014 for copending U.S. Appl. No. 13/168,229.
USPTO Notice of Allowance dated Apr. 21, 2015 for co-pending U.S. Appl. No. 13/168,349.
USPTO Office Action dated May 5, 2015 for co-pending U.S. Appl. No. 14/459,875.
USPTO Office Action dated May 7, 2015 for co-pending U.S. Appl. No. 14/337,544.
USPTO Notice of Allowance dated Jun. 3, 2014 for co-pending U.S. Appl. No. 13/168,374.
USPTO Office Action dated Jun. 5, 2014 for co-pending U.S. Appl. No. 13/168,349.
USPTO Notice of Allowance dated Jun. 17, 2014 for co-pending U.S. Appl. No. 13/168,361.
Copending U.S. Appl. No. 14/307,956, filed Jun. 18, 2014; Damon Ray Billodeaux et al.
USPTO Office Action dated Jul. 2, 2014 for co-pending U.S. Appl. No. 13/168,274.
USPTO Notice of Allowance dated Jul. 7, 2014 for co-pending U.S. Appl. No. 13/168,374.
USPTO Notice of Allowance dated Jul. 9, 2014 for co-pending U.S. Appl. No. 13/168,330.
Copending U.S. Appl. No. 14/337,544, filed Jul. 22, 2014; Daniel Latham Terrill et al.
USPTO Notice of Allowance dated Aug. 4, 2014 for co-pending U.S. Appl. No. 13/168,229.
Copending U.S. Appl. No. 14/459,875, filed Aug. 14, 2014; Damon Ray Billodeaux et al.
USPTO Notice of Allowance dated Dec. 19, 2014 for co-pending U.S. Appl. No. 13/168,374.
USPTO Notice of Allowance dated Feb. 25, 2015 for co-pending U.S. Appl. No. 13/168,274.
English translation of FR 2 906 246 A1, pp. 1-13, Mar. 2008.
USPTO Office Action dated Sep. 2, 2015 for co-pending U.S. Appl. No. 14/307,956.
USPTO Office Action dated Oct. 21, 2015 for co-pending U.S. Appl. No. 14/459,875.
USPTO Office Action dated Nov. 18, 2015 for co-pending U.S. Appl. No. 14/337,544.
USPTO Office Action dated Jan. 29, 2016 for co-pending U.S. Appl. No. 14/605,067.
V.I. Stenberg et al., "Catalytic Dehydrator. A Simplified Isolation Procedure for Acetals and Ketals," J. Org Chem., vol. 39, pp. 2815-2816 (1974).

* cited by examiner

PRODUCTION OF HYDROXY ETHER HYDROCARBONS BY LIQUID PHASE HYDROGENOLYSIS OF CYCLIC ACETALS OR CYCLIC KETALS

1. FIELD OF THE INVENTION

The invention relates to the production of hydroxy ether compounds in a liquid phase hydrogenolysis of cyclic acetals or cyclic ketals. The invention also relates to hydroxy ether compositions made in high yield.

2. BACKGROUND OF THE INVENTION

Hydroxy ether compounds have important uses as solvents, coalescents, surfactants, wetting agents, emulsifying agent, and are widely used in consumer good and industrial applications such as cleaning supplies and coating materials.

In the past, the manufacture of hydroxy ether compounds, that is compounds of the formula $ROR_2OH$, where R and $R_2$ designate substituted or unsubstituted or branched or unbranched alkyl groups, was typically accomplished by alkoxylation reactions involving alcohols and alkyl epoxides. This conventional process has proven to be somewhat inefficient, in that it produces various undesirable byproducts along with the ether alcohols. Further, it is difficult to control the number of alkylene oxide units added to the alcohol during production, resulting in undesirable molecular weight distributions. These reactions typically exhibit poor selectivity to the more desired monoether product producing a mixture of compounds of the formula $RO(R_2O)_n R_2OH$ where n is an integer from 2-8.

This selectivity issue can be addressed through hydrogenolysis of the product from acetalization reactions of aldehydes and diols, namely hydrogenolysis of cyclic acetals and cyclic ketals in the presence of a noble metal catalyst. In addition, safety concerns of dangerous alkyl epoxides can be mitigated by eliminating the need to directly handle or transport these materials. Another benefit of this technology lies in its ability to produce products from starting materials derived from renewable resources in the manufacture of 1,3-propanediol and glycerin without use of the Williamson method of synthesizing ethers which leads to low yields, high amounts of waste salt products, and requires handling of halogenated alkylating agents.

The hydrogenolysis of cyclic acetals and ketals to hydroxy ether compounds, while more selective than traditional alkoxylation, does have non-selective by-products. For example, a common by-product is formed by the reaction of one mole of acetal with one mole of hydroxy ether product, followed by hydrogenolysis to yield 1,2-dialkoxy-alkanes. This particular side reaction is a two-mole loss of starting material. Successful hydrogenolysis processes desirably reduce this side reaction as much as possible. Other detected side products include esters from internal rearrangement and ester alcohols from trans-esterification reactions.

For example, U.S. Pat. No. 4,484,009 describes the preparation of glycol monoethers by hydrogenolysis of a 2-alkyl-1,3-dioxolane with hydrogen in the presence of a noble metal catalyst such as palladium, an acid of phosphorus or ester of phosphorus as a co-catalyst, hydroquinone, and in a solvent system such as ethylene glycol.

In these processes, the use of phosphoric and other similar phosphorous-containing acid co-catalysts or halides of Group III metals and hydroquinone type additives as promoters is common. The liquid phase hydrogenolysis of cyclic acetals to ether alcohols (hydroxy ether compounds) using Ni catalyst as an active metal has met with limited success in hydrogenolysis of alkyl ethers. Such processes require handling of extra starting materials and removal of more undesirable ingredients to purify the end product. It is desirable to conduct the reaction in the absence of a co-catalyst which has difficulty in separation and lead to potential corrosion, while obtaining good selectivity to the desired hydroxy ether compound.

U.S. Pat. No. 4,479,017 describes a process for hydrogenolysis of cyclic acetals in the presence of a palladium over a carbon support and a solvent, if used, can be selected from among alcohols, ethers, and hydrocarbons.

One-pot reaction systems have also been reported, that is, reacting an aldehyde and a polyol with hydrogen in the presence of a noble metal catalyst directly to the desired ether alcohol. For example, U.S. Pat. No. 5,446,210 describes a process for the production of hydroxy ether compounds in a one pot system by reacting a polyol with an aldehyde and hydrogen in the presence of a noble metal catalyst where the molar ratio of polyol to carbonyl compound of 5:1 to 1:5 is described, but with these molar ratios, the yield was low in the range of 35 to 50% even including the bis-types of by-products with low selectivity to the mono-ether products.

US Publication No 2010/0048940 also describes a one-pot system in which a polyol and a carbonyl compound and hydrogen are reacted together in the presence of a hydrogenolysis catalyst to provide the polyol ether in which the molar ratio of polyol to carbonyl compound was at least 5:1 to improve selectivity and yield. In the one-pot system, the selectivity to the 2-butoxy ethanol from the reaction of ethylene glycol, buteraldehyde, and hydrogen reported in this publication did not exceed 90%, although reactions with diethylene glycol and tetraethylene glycol were reported to have yields of 94.5% and 91.2%, respectively. Examples of a two-stage process in which the acetal compound was first synthesized and then subjected to hydrogenolysis were reported as having even lower yields than those examples given for a single step synthesis.

In many of the examples in the literature, the processes were conducted on a batch basis. On a commercial scale unit, the process must run on a continuous basis and operated economically which requires, among other considerations, the use of a catalyst having good activity, in a process having good selectivity toward the desired hydroxy ether compound. There is a continued need to be able to carry out the efficient catalytic hydrogenolysis of cyclic compounds to make desired hydroxy ether products in high selectivity on a continuous basis, desirably without the need for co-catalysts.

3. BRIEF SUMMARY OF THE INVENTION

There is now provided a liquid phase hydrogenolysis of acetal and ketal compounds in the presence of a noble metal catalyst supported on a silica support to make hydroxy ether compounds in high selectivity without the use of acidic co-catalysts such as phosphorus based acids or stabilizers such as hydroquinone. In the process of the invention, the cyclic acetal is used as a feed to the reaction vessel for making hydroxy ether compounds.

There is provided a continuous process for making hydroxy ether compounds by hydrogenolysis comprising:
   a. feeding cyclic compounds and hydrogen to a reaction zone within a reaction vessel, wherein said cyclic compounds comprise:
      (i) cyclic acetal compounds obtained by reacting an aldehyde compound with a polyhydroxyl compound, or (ii) cyclic ketal compounds obtained by reacting a ketone compound with a polyhydroxyl compound; or
(iii) mixtures of (i) and (ii) and
b. in the reaction zone, reacting at least a portion of the hydrogen and at least a portion of the cyclic compounds in the presence of:
(i) a noble metal catalyst supported on carbon or silica and in the absence of any added acidic phosphorus compound, and
(ii) reactive solvent compounds having the same molecular formula as the polyhydroxyl compound used to make the cyclic compound fed to the reaction zone, wherein the reactive solvent compounds are present in the reaction zone at a molar ratio of reactive solvent compounds to cyclic compounds in an amount of at least 2:1,
to make a liquid reaction mixture comprising hydroxy mono-ether compounds; and
c. withdrawing the liquid reaction mixture from the reaction zone as a product stream, said product stream comprising hydroxy mono-ether compounds and at least a portion of the reactive solvent compounds.

In the process, the reaction can be conducted in the absence of a phosphorus-containing compound.

In the process, the reaction can be conducted in the absence of a stabilizer such as hydroquinone.

In the process, the reaction can be at least 90% selective toward the hydroxy mono-ether compounds.

Selectivity toward the hydroxy ether compound can be at least 80%.

4. DETAILED DESCRIPTION OF THE INVENTION

The reaction is a liquid phase reaction, meaning that the cyclic acetal or cyclic ketal compounds are in the liquid state inside the reaction zone, and desirably in the liquid state when fed to the reaction zone. The reactants fed to the reaction zone are hydrogen and cyclic acetal or cyclic ketal compounds. By subjecting cyclic acetal or cyclic ketal compounds to hydrogenolysis, the selectivity toward the hydroxy mono-ether compounds can be increased compared to a "one pot" reaction in which hydrogen is reacted with the polyhydroxyl compounds and aldehyde compounds which are the precursor materials used to make cyclic acetals.

The process of the invention is useful to make hydroxy ether compounds. Hydroxy ether compounds contain both (i) at least one ether linkage and (ii) at least one hydroxyl group. The hydroxy ether compounds represent all the reaction products of hydrogen and a cyclic acetal or ketal that have both an ether linkage and a hydroxyl group. The hydroxy ether compounds include hydroxy mono-ether compounds and if present other by-product hydrocarbons that have a hydroxyl group and an ether linkage, such as the reaction products of cyclic acetals with hydroxy mono-ether compounds.

The selectivity to the hydroxy mono-ether compounds in the process of the invention can be at least 90%, or at least 91%, or at least 92%, or at least 93%, or at least 94%, or at least 95%, or at least 96%, or at least 97%. The hydroxy mono-ether compounds also have both (i) at least one ether linkage and (ii) at least one hydroxyl group, and in addition, are those compounds in which the reaction product of cyclic acetal or cyclic ketal with one or more moles of hydrogen has not reacted any further with other cyclic acetals or cyclic ketals or other reaction products of cyclic acetals and cyclic ketals and hydrogen, and has not been subjected to a decrease in its molecular weight due to chain scission. If the cyclic acetal or ketal compound fed to the reaction zone contains 2 or more ether linkages to start, but does not react with any other cyclic acetal or cyclic ketal compounds or any other reaction products of hydrogen with cyclic acetals or cyclic ketals, it is deemed a hydroxy mono-ether compound even though more than one ether linkage is present. This is because the reaction product of hydrogen and the cyclic acetal or cyclic ketal having multiple ether linkages has not reacted any further with other cyclic acetals or with any other reaction products of hydrogen and cyclic acetals or cyclic ketals. If the reaction conditions are too harsh, some of the reaction products of hydrogen with cyclic acetals or cyclic ketals undergo chain scission after ring opening, thereby lowering its molecular weight and resulting in by-products which may not contain both an ether linkage and a hydroxyl group.

The product stream contains a hydroxy ether hydrocarbon composition which includes the hydroxy mono-ether compounds, all the other converted reaction products of hydrogen and cyclic acetals, and unreacted cyclic acetals. In one embodiment, the product stream also contains hydrogen gas.

There is now provided a liquid phase hydrogenolysis of acetal compounds with hydrogen in the presence of a noble metal catalyst to make hydroxy mono-ether compounds in high selectivity without the use of acidic co-catalysts or stabilizers such as hydroquinone. In the process of the invention, the cyclic acetal is produced and used as a feed to the reaction vessel for making hydroxy ether compounds.

In the description of the invention, mention will be made of cyclic acetals without reference to cyclic ketals for convenience, although it is understood that the invention also applies to cyclic ketals reacted to product hydroxy mono-ether compounds unless specific conditions are distinguished as applicable specially to cyclic ketals.

In the operation of the process, cyclic acetal compounds and hydrogen are fed to a reaction zone within a reaction vessel. The cyclic acetal compounds and hydrogen may be fed as separate streams without any commingling, or as a commingled stream and a separate hydrogen or cyclic acetal stream, or as separate streams which are not commingled along with a third stream that is commingled, or as single or multiple commingled streams.

The cyclic acetals are at least in the liquid state inside the reaction zone, but desirably are fed to the reaction zone as a liquid. To ensure that the cyclic acetal compounds are in the liquid state, the cyclic acetal compounds are fed to the reaction zone below the boiling point of all the cyclic acetals fed to the reaction zone at the operating pressure of the reaction zone.

Cyclic acetals are produced by reaction of an aldehyde and a polyol. Those well versed in the art can produce acetals by a number of known means. Acetals produced by any of these means can be utilized in the present invention.

Suitable cyclic acetals include any compound having a cyclic acetal moiety. The cyclic acetal moiety produced in the process of the invention has two oxygen atoms single bonded to the same carbon atom in the ring structure. Suitable cyclic acetal moieties include 1,3-dioxolane moieties and 1,3-dioxane moieties, although larger ring compounds having oxygen atoms in the 1,3 position are also contemplated.

The cyclic acetal moiety that comprises a cyclic acetal or cyclic ketal may be represented by the general Formula I:

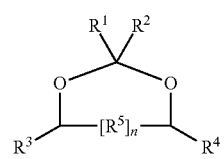

wherein $R^1$, $R^2$, $R^3$, and $R^4$ are independently H; a branched or un-branched $C_1$-$C_{50}$ alkyl, $C_2$-$C_{50}$ alkenyl, aryl-$C_1$-$C_{50}$ alkyl, aryl-$C_2$-$C_{50}$ alkenyl-, $C_3$-$C_{12}$ cycloalkyl, or a $C_3$-$C_{50}$ carboxylate ester; and wherein the alkyl, alkenyl, aryl, and cycloalkyl groups of $R^1$, $R^2$, $R^3$, and $R^4$ are optionally substituted with 1, 2, or 3 groups independently selected from —OH, halogen, dialkylamino, aldehyde, ketone, carboxylic acid, ester, ether, alkynyl, dialkylamide, anhydride, carbonate, epoxide, lactone, lactam, phosphine, silyl, thioether, thiol, and phenol;

wherein any one or both of $R^3$ and $R^4$ are optionally independently a hydroxyl, halogen, dialkylamino, amine, aldehyde, ketone, carboxylic acid, ester, ether, alkynyl, dialkylamide, anhydride, carbonate, epoxide, lactone, lactam, phosphine, silyl, thioether, thiol, or phenol;

wherein no more than one of $R^1$ or $R^2$ is H; and when only one of $R^1$ or $R^2$ is H the compound is a cyclic acetal and when neither $R^1$ nor $R^2$ is H the compound is a cyclic ketal.

wherein $R^5$ is branched or unbranched divalent alkyl or divalent alkenyl group each having 1 to 20 carbon atoms and optionally containing 1, 2, or 3 oxygen atoms in the alkyl or alkenyl group and optionally substituted with —OH, halogen, dialkylamino, aldehyde, ketone, carboxylic acid, ester, ether, alkynyl, aryl, dialkylamide, anhydride, carbonate, epoxide, lactone, lactam, phosphine, silyl, thioether, thiol, and phenol; and wherein n is an integer selected from 0 or 1.

$R^1$, $R^2$, $R^3$, and $R^4$ may independently be H, or a branched or un-branched $C_1$-$C_6$ alkyl group. Or, $R^1$, $R^2$, $R^3$, and $R^4$ may independently be H, or a branched or un-branched $C_1$-$C_4$ alkyl group. $R^1$ may be a branched or unbranched $C_1$-$C_6$ alkyl group while $R^2$ is a hydrogen atom.

$R^5$ may be a branched or unbranched divalent alkyl group having 1 to 6, or 1 to 4, or 1 to 3, or 1 to 2 carbon atoms.

Particularly useful cyclic acetals for this invention leading to useful materials of commerce include 1,3-dioxolanes having $R^1$ being an alkyl group that can lead to "E-series" type solvents. Likewise, 1,3-dioxolanes having $R^1$ being an alkyl group and $R^3$ being a methyl group can lead to "P-series" type solvents.

In the case one desires to start with a cyclic ketal compound as the starting material, then neither $R^1$ nor $R^2$ is hydrogen atoms. $R^1$ and $R^2$ may independently be a branched or un-branched $C_1$-$C_6$ alkyl group. Or, $R^1$ and $R^2$ may independently be a branched or un-branched $C_1$-$C_4$ alkyl group. Other potentially useful acetals that make use of 1,3-propylene glycol and glycerin in their preparation would include 1,3-dioxane acetals having $R^1$ being an alkyl group and 1,3-dioxane acetals having $R^1$ being an alkyl group and $R^4$ being a hydroxyl group. A variation of the glycerin acetals that have potentially useful derivatives would be 1,3-dioxolane acetals with $R^1$ being an alkyl group and $R^3$ is a hydroxymethyl group.

Examples of cyclic acetals include 2-propyl-1,3-dioxolane, 2-propyl-1,3-dioxane, 2-ethyl-1,3-dioxolane, 2-ethyl-1,3-dioxane, 2-methyl-1,3-dioxolane, 2-methyl-1,3-dixoane, 2-propyl-4-methyl-1,3-dioxane, 5,5-dimethyl-2-propyl-1,3-dioxane, 5,5-dimethyl-2-ethyl-1,3-dioxane, 2-ethyl-1,3-dioxepane, 2-ethyl-1,3,6-trioxocane, 4-methanol-2-propyl-1,3-dioxolane, or 4-methanol-2-propyl-1,3-dioxane. The specific cyclic acetal made depends on the desired end use solvent application. For example, the following cyclic acetals 2-propyl-1,3-dioxolane, 2-propyl-1,3-dioxane, 2-ethyl-1,3-dioxolane, 2-ethyl-1,3-dioxane, 2-methyl-1,3-dioxolane, 2-methyl-1,3-dioxane, 5,5-dimethyl-2-propyl-1,3-dioxane, 2-ethyl-1,3-dioxepane, 2-ethyl-1,3,6-trioxocane are suitable to make their respective solvents ethylene glycol monobutyl ether, 3-butoxy-1-propanol, ethylene glycol monopropyl ether, 3-propoxy-1-propanol, ethylene glycol monoethyl ether, 3-ethoxy-1-propanol, 3-butoxy-2,2-dimethyl-1-propanol, 4-propoxy-1-butanol, diethylene glycol monobutyl ether, 3-butoxy-1,2-propanediol, and 2-butoxy-1,3-propanediol through hydrogenolysis.

Examples of cyclic ketals that can be utilized in the present invention include, but are not limited to, 2,2-dimethyl-1,3-dioxolane, 2,2-dimethyl-1,3-dioxane, 2,2,4-trimethyl-1,3-dioxolane, 2,2-dimethyl-1,3-dioxepane, 2,2-dimethyl-1,3,6-trioxocane, 4-methanol-2,2-dimethyl-1,3-dioxolane, 2,2-dimethyl-1,3-dioxan-5-ol, 2,2,5,5-tetramethyl-1,3-dioxane, 2-ethyl-2-methyl-1,3-dioxolane, 2-ethyl-2-methyl-1,3-dioxane, 2-ethyl-2,4-dimethyl-1,3-dioxane, 2-ethyl-2-methyl-1,3-dioxepane, 2-ethyl-2-methyl-1,3,6-trioxocane, 2-ethyl-2,5,5-trimethyl-1,3-dioxane, 4-methanol-2-ethyl-2-methyl-1,3-dioxolane, 2-ethyl-2-methyl-1,3-dioxan-5-ol, 2-methyl-2-propyl-1,3-dioxolane, 2-methyl-2-propyl-1,3-dioxane, 2,4-dimethyl-2-propyl-1,3-dioxane, 2-methyl-2-propyl-1,3-dioxepane, 2-methyl-2-propyl-1,3,6-trioxocane, 2,5,5-trimethyl-2-propyl-1,3-dioxane, 4-methanol-2-methyl-2-propyl-1,3-dioxolane, 2-methyl-2-propyl-1,3-dioxan-5-ol, 2-methyl-2-pentyl-1,3-dioxolane, 2-methyl-2-pentyl-1,3-dioxane, 2,4-dimethyl-2-pentyl-1,3-dioxane, 2-methyl-2-pentyl-1,3-dioxepane, 2-methyl-2-pentyl-1,3,6-trioxocane, 2,5,5-trimethyl-2-pentyl-1,3-dioxane, 4-methanol-2-methyl-2-pentyl-1,3-dioxolane, and 2-methyl-2-pentyl-1,3-dioxan-5-ol.

The cyclic acetals and ketals are prepared by reacting a polyhydroxyl compound with a carbonyl functional compound that is either an aldehyde or a ketone, in the presence of an acid catalyst.

The polyhydroxyl compounds have at least two hydroxyl (—OH) functionalities. The polyhydroxyl compounds may contain ether or ester linkages in the longest carbon chain.

Suitable polyhydroxyl compounds for the present invention include, but are not limited to ethylene glycol, 1,2-propanediol, 1,3-propanediol, 1,4-butanediol, 1,3-butanediol, 1,2-butanediol, 1,2-pentanediol, 2,4-pentanediol, 2,2-dimethyl-1,3-propanediol, diethyleneglycol, and triethyleneglycol, glycerin, trimethylolpropane, xylitol, arabitol, 1,2- or 1,3cyclopentanediol, 1,2- or 1,3-cyclohexanediol, and 2,3-norbornanediol.

The carbonyl compounds contain at least one carbonyl functionality. In the present invention, any carbonyl compound may be used.

For example, the carbonyl compound is represented by the Formula II:

$$R^1R^2C{=}O$$

in which $R^1$ and $R^2$ are independently H, $C_1$-$C_{50}$ alkyl, $C_2$-$C_{50}$ alkenyl, aryl-$C_1$-$C_{50}$ alkyl, aryl-$C_2$-$C_{50}$ alkenyl-, or $C_3$-$C_{12}$ cycloalkyl, and wherein the alkyl, alkenyl, aryl, and cycloalkyl groups of $R^1$ are optionally saturated or unsaturated, and branched or unbranched or substituted or unsubstituted with 1, 2, or 3 groups comprising —OH, halogen, dialkylamino, $C_1$-$C_6$ alkyl, aldehyde, ketone, carboxylic acid, ester, ether, alkynyl, dialkylamide, anhydride, carbonate, epoxide, lactone, lactam, phosphine, silyl, thioether, thiol, aryl, phenol, or combinations thereof. $R^1$ and $R^2$ optionally together form a cycloalkyl having 3-12 carbon atoms.

When one of $R^1$ and $R^2$ is hydrogen, the carbonyl compound is an aldehyde compound. The aldehyde compound may, if desired, have at least one aldehyde functional group wherein the aldehyde carbon atom is bonded to a (i) branched or unbranched $C_1$-$C_9$ alkyl group or (ii) an aryl or alicyclic group which is optionally substituted with a branched or unbranched $C_1$-$C_9$ alkyl group.

Examples of aldehyde compounds include, but are not limited to, formaldehyde, benzaldehyde, acetaldehyde, propionaldehyde, butyraldehyde, isobutyraldehyde, pentaldehyde, 2-methylbutyraldehyde, 3-methylbutyraldehyde, n-pentanal, isopentanal, hexaldehyde, heptaldehyde, 2-ethylhexaldehyde, octanal, nonanal, n-decanal, 2-methylundecanal, lauryl aldehyde, myristyl aldehyde, cetyl aldehyde, stearyl aldehyde, behenyl aldehyde, glutaraldehyde, acrolein, crotonaldehyde, oleyl aldehyde, linoleyl aldehyde, linolenyl aldehyde, erucyl aldehyde, cinnamaldehyde, 1,3-cyclohexanedicarboxaldehyde, 1,4-cyclohexanedicarboxaldehyde, and combinations thereof.

Suitable polyols for the present invention include, but are not limited to, ethylene glycol, 1,2-propanediol, 1,3-propanediol, 1,4-butanediol, 1,3-butanediol, 1,2-pentanediol, 2,2-dimethyl-1,3-propanediol, diethyleneglycol, triethyleneglycol, and glycerol (glycerin).

Preferably, the aldehyde compound is 2-ethylhexaldehyde or an aliphatic aldehyde compound wherein the aldehyde carbon atom is bonded to a branched or unbranched $C_1$-$C_5$ alkyl group (for a total of 2-6 carbon atoms). Examples of the latter compounds include acetaldehyde, propionaldehyde, butyraldehyde, isobutyraldehyde, pentaldehyde, 2-methylbutyraldehyde, 3-methylbutyraldehyde, hexaldehyde, benzaldehyde, 2-ethylhexaldehyde, octanal, and nonanal.

Examples of suitable ketone compounds include, but are not limited to, acetone, methyl isobutyl ketone (2-butanone), methyl ethyl ketone, methyl propyl ketone (2-pentanone), methyl isopropyl ketone (3-methyl-2-butanone), methyl isobutyl ketone (4-methyl-2-pentanone), 2-hexanone, cyclohexanone, 2-heptanone(methyl amyl ketone), 4-heptanone, and 2-octonone.

In the process of the invention for making hydroxy mono-ether compounds, cyclic acetal or cyclic ketal compounds and hydrogen are fed to a reaction zone within a reaction vessel. The cyclic acetal or cyclic ketal compounds can be fed as a first stream and hydrogen as a second stream separately from the cyclic acetals, or a portion of all of the cyclic acetals may be mixed with hydrogen gas and fed as a combined stream to the reaction vessel. The cyclic acetal stream may be fed at a location within the top half of the reaction vessel and the hydrogen stream fed within the bottom half of the reaction vessel and allowed to contact each other in a countercurrent flow. The liquid acetals may be in the form of a liquid within the reaction zone and flow in a downward direction in a vertical column over one or more catalyst beds while hydrogen gas rises in an upward direction. Alternatively, both the first and second streams are fed into a reaction vessel and the upper half of the reaction vessel having an L/D of over 3:1, or over 4:1, or over 5:1, or over 6:1, or over 7:1, and allowed to contact each other in a co-current flow.

Instead of a vertical vessel, one may use a horizontal vessel having a fixed catalyst bed into which the first and second streams are fed to the reaction zone within the vessel within a first vertically divided quadrant among four equal quadrants and the hydroxy mono-ether products flow out the reaction zone within the vessel at a location from the third or fourth quadrants. The reactor design is not crucial for the operation of this invention. The reactor should be designed to permit a gaseous mixture of hydrogen and the cyclic acetal compounds to pass over the supported noble metal catalyst and exit the reactor zone with the desired hydroxy ether compound as a product mixture. Those versed in the art can determine appropriate reactor schemes, by continuous stirred tanks, plug flow reactors such as long tubular designs and multi-tube short path designs, or down flow trickle beds are examples. Other convenient designs include "pancake" reactors have a wide continuous catalyst bed that is of a relatively short path. The process can also be conducted in exotic designs such as spinning basket or Berty type reactors can be used. A continuous stirred tank (CSTR) or Buss Loop reactor can also be used. Desirably, down flow trickle beds are used.

The first stream can be introduced into the reaction vessel at ambient temperature. Alternatively, the first stream can be preheated. The pre-heating temperature may range from above 25° C., or at least 40° C., or at least 50° C., or at least 60° C., or at least 100° C., or at least 130° C., or at least 150° C., and up to 250° C., or up to 225° C., or up to 200° C., or up to 180° C.

The second stream comprising hydrogen may be fed into the reaction vessel at 25° C. or ambient condition, and at any other temperature suitable for the first stream. The hydrogenolysis reaction uses hydrogen as both a gaseous feed medium and reactant in this invention. Hydrogen is used to cleave the carbon-oxygen bond of either the 1,2 carbon-oxygen bond or the 2,3-carbon-oxygen bond by means of the supported noble metal catalyst. The purity of the hydrogen being fed to the reactor is high enough to effect the desired reaction and not contain significant amounts of impurities that could act as poisons or inhibitors. Inert hydrocarbons such as methane, ethane, propane and butane are managed by normal gas purging methods to keep the desired partial pressure of reactant hydrogen present in the reactor. For certain impurities such as carbon monoxide, methods such as nickel methanation catalyst beds and the like can be used to convert this poison into an inert methane impurity and thereby control the concentration of CO in the reactor feed stream.

The molar ratio of hydrogen to all cyclic acetal compounds can be at least 1:1, or at least 2:1, and up to 100:1, or up to 20:1, or up to 10:1, or up to 5:1. In most cases, this ratio will be from 1:1 to 5:1.

The reactor pressures used may be from one atmosphere absolute (or 0 psig or 0 kPa gauge), or from at least 5 atm, or from at least 8 atm, or from at least 10 atm, or from at least 12 atm, or from at least 13 atm, or from at least 15 atm, or from at least 20 atm (about 300 psig), or at least 28 atm (400 psig) and up to 141 atmospheres (2000 psig), or up to 105 atmospheres (1500 psig), or up to 88 atmospheres (1250 psig), or up to 69 atmospheres (or 1000 psig, or 6895 kPa) or up to 51 atmospheres (or 750 psig, or 5171 kPa gauge), or up to 45 atm, or up to 40 atm, or up to 35 atm, or up to 30 atm, or up to 27 atm, or up to 25 atm, or up to 10 atm. Suitable reactor pressures can range from at least 10 atm, or at least 13 atm, and up to 141 atm, or up to 105 atm, or up to 88 atm. One example of a suitable range is from 13 atm to 141 atm (200 to 2000 psig), or 20 atm (300 psig) to 88 atm (1250 psig), for many practical operations.

Once inside the reaction zone, hydrogen and liquid cyclic acetal or cyclic ketal compounds are reacted in the presence of a solvent and a heterogeneous noble metal catalyst supported on carbon or silica to make a reaction mixture containing hydroxy mono-ether compounds.

The cyclic acetal is contacted with hydrogen over a supported metal catalyst to generate a hydroxy ether compound through cleavage of a carbon-oxygen bond—a process known as hydrogenolysis. The resulting product is described by the general Formula III shown below:

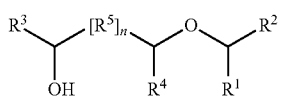

wherein $R^1$, $R^2$, $R^3$, $R^4$, and $R^5$ and n are as described above.

The hydrogenolysis reaction is carried out in the reaction zone in a mixed gas/liquid phase, with the cyclic acetal or cyclic ketal compounds being in the liquid phase.

The selectivity to the desired hydroxy mono-ether compound can be obtained by diluting the acetal or ketal feed in a liquid reactive solvent that has the same molecular formula as the polyhydroxyl compound used to make the cyclic acetal or cyclic ketal compound at a molar ratio of polyhydroxyl compound to cyclic compound of at least 2:1. The reaction desirably proceeds in the presence of this liquid solvent for the hydroxy mono-ether compounds. For example, if the cyclic acetal or ketal was made by reacting ethylene glycol with an aldehyde or ketone compound, it is desirable to use ethylene glycol as the reactive solvent in the hydrogenolysis of the cyclic acetal or cyclic ketal to minimize the formation of by-products, and further ethylene glycol is readily removed from the product stream.

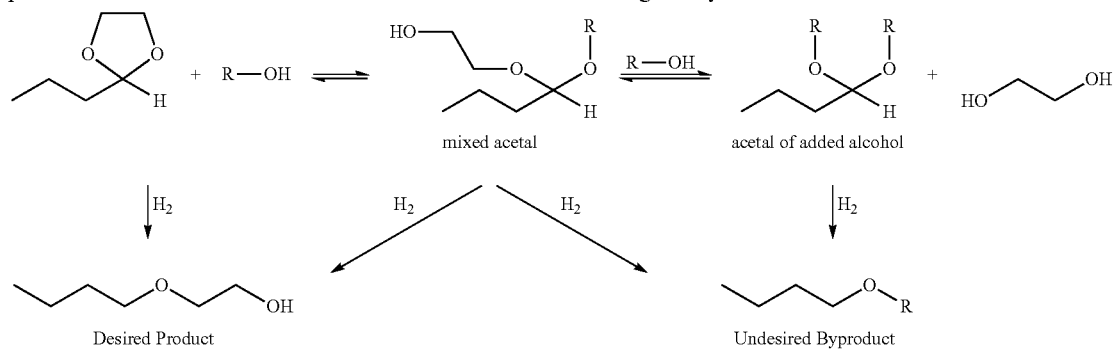

The PDX acetal in this example is a reactive molecule, and if this reaction were conducted in the presence of an alcohol (such as methanol, ethanol, etc.) as a reactive solvent, then the acetal would react with this alcohol at some rate forming two new acetals: a mixed acetal and an acetal of the solvent alcohol. The mixture of these three acetals under hydrogenolysis would be converted into two products: the desired ether alcohol (EB) and the ether of the solvent alcohol with the starting aldehyde:

We have found that the reactive solvent that has the same molecular formula as the polyhydroxyl compound used to make the cyclic compound, when used in a stoichiometric excess of polyhydroxyl compound of at least 2:1, increases the selectivity toward the production of the desired hydroxy mono-ether compound. To illustrate, the production of ethylene glycol butyl ether ("EB") made from 2-propyl-1,3-dioxolane ("PDX") will be used as an example.

The overall scheme for converting butyraldehyde to PDX to EB is as follows:

Use of non-alcohol solvents would not cause byproduct formation in the same way as an alcohol solvent; however, similar byproduct formation would still be problematic. This is because the ether alcohol product of acetal hydrogenolysis (EB) is an alcohol and as such will also react with the acetal in the same manner as an alcohol added as a solvent. As the concentration of the product ether alcohol (EB) increases it reacts with the acetal (PDX) and undergoes hydrogenolysis to make a byproduct diether, thereby also diminishing selectivity:

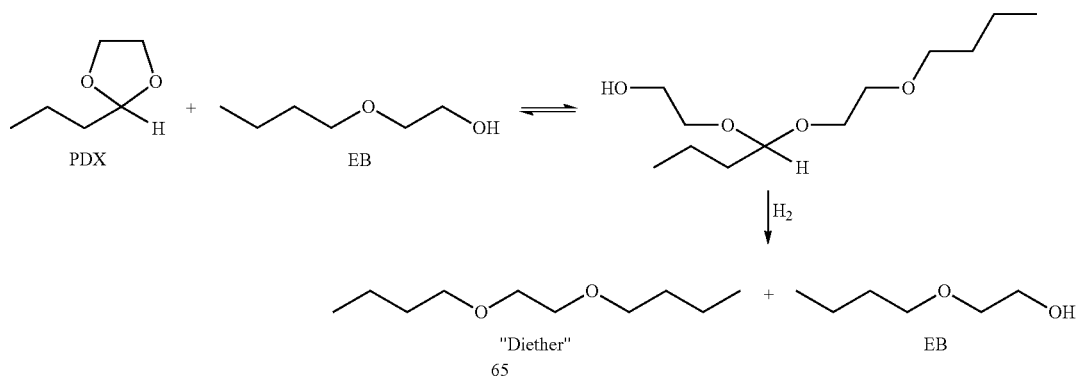

Selectivity can be enhanced and the formation of the diether can be minimized by perturbing the equilibrium that leads to its formation. This can be done by adding to the cyclic acetal or ketal during hydrogenolysis a reactive solvent that has the same molecular formula as the polyhydroxyl compound used to make the cyclic acetal or ketal and by using a stoichiometric excess (at least 2:1) of this type of reactive solvent relative to the cyclic compound. This type of reactive solvent is exclusively defined for each acetal that undergoes hydrogenolysis. In the case of PDX the alcohol must be ethylene glycol. This is because the method for minimizing diether formation is to use the ethylene glycol from acetal synthesis to shift the equilibrium amounts of intermediates in the hydrogenolysis reaction to mostly species that form the desired hydroxy mono-ether compound:

Suitable noble metal catalyst sizes can be at least at least 1 nm, or at least 2 nm, or at least 3 nm, or at least 4 nm, and can be up to 50 nm, or up to 30 nm, or up to 20 nm, or up to 10 nm. The particle size values are average particle sizes. Those within a range of 2-10 nm are useful.

The surface area of the carbon or silica support can be within a range of 10 m$^2$/g to 100 m$^2$/g, and the noble metal average particle size can be within a range of 2 to 10 nm.

The reaction is carried out in the absence of any acidic phosphorus compounds added to the feeds or added to the reaction zone. In one embodiment, the reaction is carried out in the absence of any added acidic catalyst promoters, and in another embodiment, the reaction is carried out in the absence of any added co-catalyst or promoter compounds. In yet another embodiment, the reaction is carried out with a sole

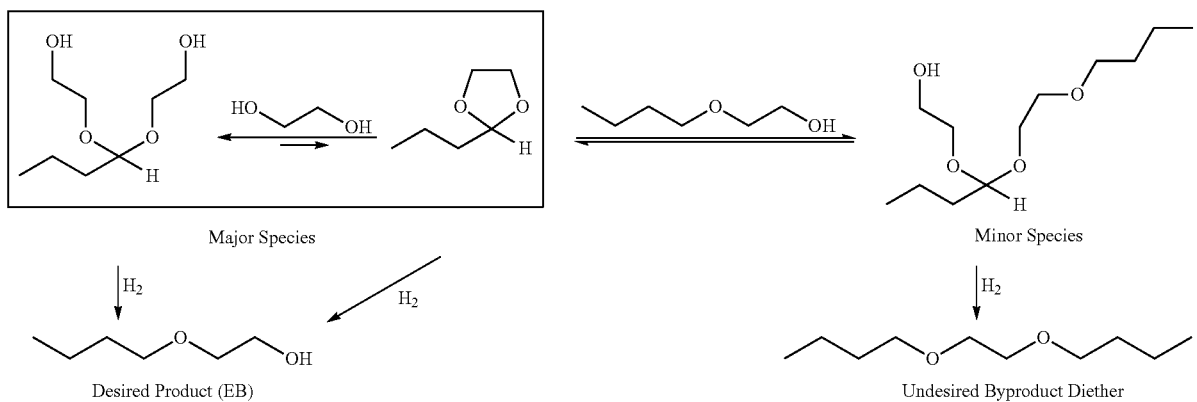

Major Species

Desired Product (EB)

Minor Species

Undesired Byproduct Diether

The amount of reactive solvent used in this invention that is fed to the reaction zone relative to all solvents or diluents fed to the reaction zone can be at least 50%, or at least 75%, or at least 80%, or at least 90%, or at least 95%, or at least 97%, or at least 98%, or at least 99%, or 100% by weight based on the weight of all solvents and diluents.

The molar ratio of reactive solvent used in the invention to cyclic acetal or cyclic ketal compounds is at least 2:1. Suitable amounts in excess of 2:1 are at least 3:1, or at least 4:1, or at least 5:1, or at least 7:1, or at least 9:1, or at least 10:1, or at least 15:1, or at least 18:1, or at least 20:1, and up to 50:1, or up to 25:1, or up to 20:1, or up to 15:1, or up to 10:1, or up to 9:1, or up to 5:1. In another embodiment, the solvent/acetal molar ratio is from 3:1 to 20:1, or 4:1 to 20:1, or 5:1 to 20:1, or 9:1 to 20:1.

A large number of supported noble metal catalysts can be employed in this invention and are preferred over base metal catalysts such as reduced nickel, copper or cobalt. We have also found that of the noble metals, palladium is most desirable for use in this invention although other noble metals like Ru, Rh, Pt, Ir, and Os may be used in varying degrees of effectiveness.

The metal is loaded onto a carbon or silica support, which, in combination with the reactive solvent compound, are particularly effective to obtain hydroxy mono-ether compounds in higher selectivity.

It is desired to use a fixed catalyst bed so as to avoid removing large quantities of catalyst from the product stream.

The noble metal can be loaded on the catalyst support in concentrations of at least 0.1%, or at least 0.3%, or at least 0.5%, and up to 50% by total weight, or up to 10%, or up to 5%, or up to 4%, or up to 3%, or up to 2%. The metal concentration can be between 0.5% and 10%, or between 0.5% and 2%.

catalyst that is the noble metal catalyst supported on carbon or silica and no other catalysts or catalyst promoters.

The hydrogenolysis is carried out at temperatures of at least 100° C., or at least 120° C., or at least 150° C., or at least 170° C. and up to 300° C., or up to 250° C., or up to 225° C., or up to 210° C., or up to 200° C. For example the temperature may range from 150° C. to 225° C., or 150° C. to 200° C.

In the process of the invention, a product stream is withdrawn from the reaction zone, said product stream comprising hydroxy mono-ether compounds such as those set forth in Formula III above. Other ingredients in the product stream include unreacted cyclic acetal compounds, by-products, hydrogen, solvent, and sometimes trace amounts of noble metal catalyst.

In one embodiment, the product stream is rich in reactive solvent, meaning that the highest concentration of any ingredient in the product stream in the liquid phase is reactive solvent.

Examples of product stream compositions are as set forth in Table A below illustrating the wt % ranges for each ingredient in the product stream(s), wherein the stated weight percentages are based on the weight of all liquid ingredients within all the liquid product stream(s) as withdrawn from the reaction zone without any further refining or purification or processing:

TABLE A

| Ingredient | Wt % Range | Wt % Range | Wt % Range |
|---|---|---|---|
| Reactive Solvent | 75%-95%% | 80-90% | 80-85% |
| Hydroxy Ether | 1-20% | 5-10%% | 10-15% |
| Mono-Hydrocarbons | | | |

TABLE A-continued

| Ingredient | Wt % Range | Wt % Range | Wt % Range |
| --- | --- | --- | --- |
| By-Products | 0-15%% | 0-10%% | 0-0.5% |
| Unreacted Cyclic acetal or cyclic ketal compounds | 0-15% | 0-10% | 0-1%% |
| Catalyst | 0-2% | 0.5-1.8% | 1-1.6% |
| *Selectivity | 90%-100% | 95-100% | 97-100% |

*Selectivity To The Hydroxy Ether Mono-hydrocarbons

The yield of the hydroxy mono-ether compound (not by-products or water) is determined by dividing the moles of hydroxy mono-ether compound produced by the moles of cyclic compounds fed, multiplied by 100.

Selectivity to hydroxy mono-ether compound is determined by dividing the moles of hydroxy mono-ether compound produced by the moles of their respective cyclic compounds converted, multiplied by 100.

Conversion of cyclic compounds is determined by dividing the moles of cyclic compounds converted by the moles of the respective cyclic compounds fed, multiplied by 100.

The invention is capable of producing hydroxy mono-ether compounds to a high selectivity. For example, the selectivity of the converted compounds to hydroxy mono-ether compounds (and not the by-products) can be at least 80%, or at least 85%, or at least 90%, or at least 93%, or at least 95%, or at least 96%, or at least 97%, or at least 98%, and up to less than 100%, or up to less than 99%, or up to 98%.

The conversion rates from the cyclic compounds to any and all converted reaction products of cyclic acetal compounds can be at least 40%, or at least 50%, or at least 70%, or at least 80%, or at least 85%, or at least 90%, or at least 91%, or at least 92%, or at least 95%, or at least 96%, or at least 97%, or at least 98%, and up to less than 100%, or up to less than 99%, or up to 98%, or up to 97%, or up to 96%, or up to 95%.

The yield of hydroxy mono-ether compounds in the process of the invention can be at least 50%, or at least 60%, or at least 70%, or at least 80%, or at least 85%, or at least 90%, or at least 91%, or at least 92%, or at least 93%, or at least 94%, or at least 95%, or at least 96%, or at least 97%, or at least 98%, and up to less than 100%, or up to less than 99%, or up to 98%, or up to 97%. These yield values are obtainable even to make 2-butoxyethanol.

The process of the invention is capable of selectively generating hydroxy mono-ether compounds at good conversion rates even when the reaction in the reaction zone proceeds in the absence of a phosphorus containing promoter and even in the absence of a metal co-catalyst or any other catalyst promoter. For example, phosphoric acid, alkyl phosphoric acid, phosphoric esters, pyrophosphoric acid, metaphophoric acid, and pyrophosphoric esters have been thought to be useful, and some have been used, as a catalyst promoter to increase the conversion rates and activity of a palladium catalyst. The hydrogenolysis reaction in the reaction zone can proceed in the presence of a supported single catalyst system at high selectivity and high conversion rates instead of the frequently used supported co-catalyst system. By using a supported single catalyst system, there is no acid co-catalyst, which washes out into the product stream and requires removal.

The process of the invention is also capable of selectively generating hydroxy mono-ether compounds even when the reaction in the reaction zone proceeds in the absence of a stabilizer such as hydroquinone. Stabilizers have been thought useful to increase the selectivity of the reaction toward the hydroxy mono-ether species. In the present invention, however, using a palladium noble metal catalyst on a carbon or silica support, the influence of hydroquinone on increasing selectivity is not observed. Thus, one may advantageously proceed in the hydrogenolysis reaction with high selectivity without the necessity for removing hydroquinone from the product stream.

The product hydroxy ether compound can be separated from the product stream by any typical means. Examples of such techniques include decantation, extraction, crystallization, evaporation, and fractional distillation after removal of the catalyst by techniques such as filtration.

The process of the invention may be run in a batch mode, a semi-continuous mode, or a continuous mode.

EXAMPLES

Examples 1-6

Production of 2-butoxyethanol (EB)

100 g of ethylene glycol (EG) and 20 g of 2-propyl-1,3-dioxolane (PDX) were combined in a 300 mL autoclave with 0.50 g of 5% (by weight) Pd on carbon catalyst. The autoclave was sealed and purged twice with $N_2$ and once with $H_2$. The reactor was charged with $H_2$ and heated to 150° C. The reactor was then brought to an operating pressure of 6.89 MPa and stirring commenced at 750 rpm. Pressure was maintained through the duration of the experiment. After 2 h, the autoclave was cooled and remaining gas vented. The autoclave was opened, its contents filtered, and the filtrate analyzed by gas chromatography (GC). 96.3% conversion of PDX and 97.3% selectivity to EB were observed. The only non-selective product observed was 1,2-dibutoxyethane (EG dibutyl ether).

Results from Examples 2-6, carried out in a similar manner, are presented in Table 1.

TABLE 1

| Example | Temperature (° C.) | Pressure (MPa) | Catalyst Loading (g) | Reaction Time (h) | PDX Conversion | EB Selectivity |
| --- | --- | --- | --- | --- | --- | --- |
| 2 | 200 | 2000 | 0.75 | 2 | 96.6% | 97.2% |
| 3 | 200 | 1000 | 0.50 | 2 | 89.6% | 97.9% |
| 4 | 100 | 1000 | 0.50 | 2 | 12.3% | 99.5% |
| 5 | 200 | 500 | 1.0 | 2 | 84.2% | 90.0% |
| 6 | 200 | 500 | 1.0 | 1 | 79.4% | 94.4% |

Comparative Examples 1-7

These examples contained phosphoric acid co-catalyst and a hydroquinone stabilizer. In most cases, selectivity was not improved by the addition of acid or hydroquinone.

Comparative Example 1

100 g of EG and 20 g of PDX were combined in a 300 mL autoclave with 0.50 g of 5% (by weight) Pd on carbon catalyst. 72 mg of 85% phosphoric acid and 12 mg of hydroquinone (HQ) co-catalysts were added. The autoclave was sealed and purged twice with $N_2$ and once with $H_2$. The reactor was charged with $H_2$ and heated to 150° C. The reactor was then brought to an operating pressure of 10.3 MPa with stirring. After 3 h, the autoclave was cooled and vented. Autoclave contents were filtered, and the filtrate analyzed by gas chromatography (GC). 74.1% conversion of PDX and 91.8% selectivity to EB were observed.

Results from Comparative Examples 2-7 carried out under similar conditions are presented in Table 2.

TABLE 2

| Comparative Example | Temperature (° C.) | Pressure (MPa) | Catalyst Loading (g) | $H_3PO_4$ (mg) | HQ (mg) | Reaction Time (h) | PDX Conversion | EB Selectivity |
|---|---|---|---|---|---|---|---|---|
| 2 | 200 | 3.44 | 1 | 74 | 0 | 1 | 94.8% | 85.8% |
| 3 | 200 | 3.44 | 1 | 75 | 0 | 0.5 | 81.1% | 85.1% |
| 4 | 200 | 2.41 | 1 | 72 | 0 | 1 | 52.6% | 79.9% |
| 5 | 150 | 3.44 | 1 | 72 | 0 | 1 | 38.5% | 90.4% |
| 6 | 200 | 6.89 | 1.0 | 0 | 12 | 2 | 92.8% | 91.1% |
| 7 | 200 | 6.89 | 0.5 | 72 | 12 | 2 | 92.8% | 92.7% |

Comparative Examples 8-9

These examples were carried out in similar manner to Comparative Examples 1-7 except palladium on alumina was substituted for palladium on carbon. The conversion in these examples was much lower than that of carbon supported Pd catalysts.

TABLE 3

| Comparative Example | Temperature (° C.) | Pressure (MPa) | Catalyst Loading (g) | $H_3PO_4$ (mg) | HQ (mg) | Reaction Time (h) | PDX Conversion | EB Selectivity |
|---|---|---|---|---|---|---|---|---|
| 8 | 150 | 10 | 0.5 | 70 | 10 | 3 | 9.1% | 97.9% |
| 9 | 150 | 13.8 | 1.0 | 75 | 10 | 3 | 10.0% | 97.5% |

Example 8

Production of 2-propoxyethanol (EP)

100 g of EG and 20 g of 2-ethyl-1,3-dioxolane (EDX) were combined in a 300 mL autoclave with 1.0 g of 5% (by weight) Pd on carbon catalyst. The autoclave was sealed and purged twice with $N_2$ and once with $H_2$. The reactor was charged with $H_2$ and heated to 200° C. The reactor was then brought to an operating pressure of 3.44 MPa and stirring commenced at 750 rpm. Pressure was maintained through the duration of the experiment. After 1 h, the autoclave was cooled and remaining gas vented. The autoclave was opened, its contents filtered, and the filtrate analyzed by gas chromatography (GC). The reactor contained 0.52 g of EDX, 16.4 g of EP, 5.86 g of 1,2-dipropoxy-ethane, 0.51 g of mono propionate ester of EG, and 100.9 g of EG. This result corresponds to 97.4% conversion of acetal and 82.6% selectivity to EP.

Example 9

Production of 2-(2-ethylhexyloxy)ethanol 100 g of EG and 20 g of 2-(1-ethyl-pentyl)-1,3-dioxolane were combined in a 300 mL autoclave with 1.5 g of 5% (by weight) Pd on carbon catalyst. The autoclave was sealed and purged twice with $N_2$ and once with $H_2$. The reactor was charged with $H_2$ and heated to 200° C. The reactor was then brought to an operating pressure of 6.89 MPa and stirring commenced at 750 rpm. Pressure was maintained through the duration of the experiment. After 1 h, the autoclave was cooled and remaining gas vented. The autoclave was opened and its contents filtered. The filtrate separated into two layers with an EG rich layer on the bottom and an organic 2-(2-ethylhexyloxy)ethanol rich layer on top. The two layers were analyzed by gas chromatography (GC) and the combined results from those analyses showed 4.82 g of dioxolane, 12.5 g of 2-(2-ethylhexyloxy)ethanol, 0.77 g of diether, 0.40 g of 2-ethyl-hexanol, and 101 g of EG. This corresponds to a 76.5% conversion of acetal and 78.6% selectivity to the desired ether alcohol.

Example 10

Synthesis of 3-ethoxy-propanol (3-EP)

100 g of 1,3-propanediol and 20 g of 2-methyl-1,3-dioxane were combined in a 300 mL autoclave with 1.0 g of 5% (by weight) Pd on carbon catalyst. The autoclave was sealed and purged twice with $N_2$ and once with $H_2$. The reactor was charged with $H_2$ and heated to 200° C. The reactor was then brought to an operating pressure of 6.89 MPa and stirring commenced at 750 rpm. Pressure was maintained through the duration of the experiment. After 1 h, the autoclave was cooled and remaining gas vented. The autoclave was opened, its contents filtered, and the filtrate analyzed by gas chromatography (GC). The reactor contained 0.68 g of 2-methyl-1,3-dioxane, 18.1 g of 3-EP, 0.39 g of 1,3-diethoxypropane, 0.46 g of ethanol, 2.7 g of water, and 99.9 g of 1,3-propanediol. This corresponds to a 97.4% conversion of 2-methyl-1,3-dioxane and 92.1% selectivity to 3-EP.

Example 11

Synthesis of 3-propoxy-propanol (3-PP)

100 g of 1,3-propanediol and 20 g of 2-ethyl-1,3-dioxane were combined in a 300 mL autoclave with 1.0 g of 5% (by weight) Pd on carbon catalyst. The autoclave was sealed and purged twice with $N_2$ and once with $H_2$. The reactor was charged with $H_2$ and heated to 200° C. The reactor was then brought to an operating pressure of 6.89 MPa and stirring commenced at 750 rpm. Pressure was maintained through the duration of the experiment. After 1 h, the autoclave was cooled and remaining gas vented. The autoclave was opened, its contents filtered, and the filtrate analyzed by gas chromatography (GC). The reactor contained 5.06 g of 2-ethyl-1,3-dioxane, 11.8 g of 3-PP, 0.93 g of 1,3-dipropoxypropane, and 102 g of 1,3-propanediol. This corresponds to a 75% conversion of 2-ethyl-1,3-dioxane and 92.7% selectivity to 3-PP were observed.

Example 12

Production of 3-butoxy-propanol (3-BP)

600 g of 1,3-propanediol and 140 g of 2-propyl-1,3-dioxane were combined in a 2 L stainless steel autoclave. 3.5 g of 5% Pd on carbon catalyst and 500 mg of 85% phosphoric acid co-catalyst were added. The reactor was sealed and purged twice with $N_2$ and once with $H_2$. The reactor was charged with $H_2$ and heated to 200° C. The reactor was brought to an operating pressure of 6.89 MPa and stirring commenced at 750 rpm. Temperature and pressure were maintained for 2 h. The reactor was cooled, vented, and the contents filtered. The filtrate was analyzed by GC to yield 135.1 g of 3-BP, 11.1 g of 1,3-dibutoxypropane, and 594 g of 1,3-propanediol. This corresponds to 100% conversion of the acetal and 92% selectivity to the desired ether alcohol, 3-BP.

Example 13

Production of 3-butoxy-propanol (3-BP)

1000 g of 1,3-propanediol and 500 g of 2-propyl-1,3-dioxane were combined in a 2 L stainless steel autoclave with 6.0 g of 5% Pd on carbon catalyst. The reactor was sealed and purged twice with $N_2$ and once with $H_2$. The reactor was charged with $H_2$ and heated to 200° C. The reactor was brought to an operating pressure of 6.89 MPa and stirring commenced at 750 rpm. Temperature and pressure were maintained for 2 h. The reactor was cooled, vented, and the contents filtered. The filtrate was analyzed by GC to yield 153 g of 2-propyl-1,3-dioxane, 288 g of 3-BP, 15.9 g of 1,3-dibutoxypropane, and 1017 g of 1,3-propanediol. This corresponds to yield 69% conversion of the acetal and 95% selectivity to the desired ether alcohol, 3-BP.

Example 14

Synthesis of 3-butoxy-2,2-dimethyl-propanol 90 g of 2,2-dimethyl-1,3-propanediol, 10 g of water, and 20 g of 5,5-dimethyl-2-propyl-1,3-dioxane were combined in a 300 mL autoclave with 1.5 g of 5% (by weight) Pd on carbon catalyst and 100 mg of phosphoric acid. The autoclave was sealed and purged twice with $N_2$ and once with $H_2$. The reactor was charged with $H_2$ and heated to 200° C. The reactor was then brought to an operating pressure of 10.3 MPa and stirring commenced at 750 rpm. Pressure was maintained through the duration of the experiment. After 2 h, the autoclave was cooled and remaining gas vented. The autoclave was opened, its contents filtered, and the filtrate analyzed by gas chromatography (GC). 94% conversion of the acetal and 99% selectivity to 3-butoxy-2,2-dimethyl-propanol were observed.

Example 15

Production of 3-butoxy-1,2-propanediol 16.6 g of an equimolar mixture of cis/trans-4-hydroxymethyl-2-propyl-1,3-dioxolane and 5-hydroxy-2-propyl-1,3-dioxane were combined with 100 g of glycerin (glycerol) in a 300 mL stainless steel autoclave. 2.0 g of 5% Pd/C catalyst were added and the autoclave was sealed. The reactor was heated to 200° C. The reactor was then brought to an operating pressure of 6.89 MPa and stirring commenced at 750 rpm. Pressure was maintained through the duration of the experiment. After 2 h, the autoclave was cooled and remaining gas vented. The autoclave was opened, its contents filtered, and the filtrate analyzed by gas chromatography (GC). 76% conversion of the acetal mixture was observed. Upon analysis of the results, the mixture was found to demonstrate 26.1% selectivity to 2-butoxy-1,3-propanediol, 71.7% 3-butoxy-1,2-propanediol, and the balance n-butanol.

Examples 16-19

Production of 2-butoxy-propanol

Into a 300 mL stirred autoclave were loaded 20 g 4-methyl-2-propyl-1,3-dioxolane (0.15 mol), 100 g 1,2-propanediol (1.3 mol) and 2 g 5% Pd/C (Degussa E101 N0/W). The autoclave was purged two times with 1.3 MPa $H_2$ and then pressurized to half the desired reaction pressure. Agitation (750 rpm) was started and the reaction was heated to the desired reaction temperature. Upon reaching the desired temperature, $H_2$ pressure was increased to the final set point. $H_2$ pressure was maintained by use of a surge tank. After 60 minutes, the heating was stopped and when the reaction reached ambient temperature, the pressure was released. The reaction was analyzed by gas chromatography mass spectrometry. Conversion of 4-methyl-2-propyl-1,3-dioxolane and the relative ratio of hydrogenolysis to 2-butoxypropan-1-ol versus 1-butoxypropan-2-ol are presented in Table 4.

TABLE 4

| Example | Temperature °C. | Pressure MPa | 4-methyl-2-propyl-1,3-dioxolane conversion | 2-butoxypropan-1-ol: 1-butoxypropan-2-ol |
|---|---|---|---|---|
| 16 | 200 | 6.89 | 96% | 52:48 |
| 17 | 150 | 6.89 | 97% | 55:45 |
| 18 | 100 | 6.89 | 66% | 58:42 |
| 19 | 200 | 3.45 | 87% | 51:49 |

Comparative Example 10

This example compares the two-step process to the one-step process. Into a 300 mL stirred autoclave were loaded 12.4 g butyraldehyde (0.17 mol), 111 g ethylene glycol (1.78 mol) and 2 g 5% Pd/C (Degussa E101 N0/W). The autoclave was purged two times with 200 MPag $H_2$ and then pressurized to 3.45 MPa $H_2$. Agitation (750 rpm) was started and the reaction was heated to 200° C. Upon reaching the set temperature $H_2$ pressure was increased to 1000 MPag. $H_2$ pressure was maintained by use of a surge tank. After 60 minutes, the heating was stopped and when the reaction reached ambient temperature, the pressure was released. The reaction was analyzed by gas chromatography. Conversion of butyraldehyde was 99.7% with an EB selectivity of 53.8% and a butanol selectivity of 14.0%.

Example 20

Production of 2-isobutoxy-propanol 20 g of 2-isopropyl-1,3-dioxolane and 100 g of ethylene glycol were combined in a 300 mL stainless steel autoclave.

2.0 g of 5% Pd/C catalyst were added and the autoclave was sealed. The reactor was heated to 200° C. The reactor was then brought to an operating pressure of 3.45 MPa and stirring commenced at 750 rpm. Pressure was maintained through the duration of the experiment. After 2 h, the autoclave was cooled and remaining gas vented. The autoclave was opened, its contents filtered, and the filtrate analyzed by gas chromatography (GC). 83% conversion of the acetal mixture was observed. Upon analysis of the results, the mixture was found to demonstrate 95.8% selectivity to 2-isobutoxy-ethanol.

Examples 21-28

These were carried out using a continuous flow trickle bed reactor.

The reactor was constructed of a 122 cm long by 1.9 cm O.D. piece of stainless steel tubing. The reactor was hung vertically in an Applied Test System Model 3210 Split Tube Furnace which consists of one 3-zone 120 volt furnace with 92 cm of internal heat zone and an overall length of 101.6 cm. Each zone had a Type K thermocouple (TC) and separate controls. The reactor had two 46 cm K-type thermocouples imbedded in the top and the bottom of the reactor. Each thermocouple extended 1.3-2.5 cm into the catalyst bed. The reactor was controlled by a Delta V process control system.

The reactor contained a catalyst support screen held in place 45.7 cm from the bottom of the reactor by a piece of 0.64 cm O.D. stainless steel tubing. 40 mL of catalyst was packed onto the screen resulting in a bed approximately 20.3 cm in height. 3 mm glass balls were used to pack the rest of the reactor.

A dual liquid feed system was utilized. EG was fed from a 5-gallon stainless tank through an Eldex pump. PDX was fed through an ISCO syringe pump. Both liquids traveled through 0.64 cm stainless steel tubing and mixed at a joining "tee". The combined liquids traveled through a single piece of 0.64 cm tubing and mixed with $H_2$ before entering the top of the reactor.

Gas feeds were raised from 1.7 MPa to operating pressure through use of an air driven gas compressor. Compressed gas was stored in a vertically mounted pressure tank with a maximum rating of 3000 MPa. Gas feeds were maintained at 1.3 MPa above operating pressure. Gas feeds were managed via Model 5850i Brooks Mass Flow controllers. Pressure was maintained through a pressure control valve. A shell-in-tube heat exchanger was present and had a 50:50 mix of glycol and water as the cooling media. This glycol was pumped from a temperature controlled circulating bath. Cooled reactor effluent was collected in a 38-L tank, which had an armored sight glass with a gas take-off. A back-pressure regulator was located after the sight glass and was configured to vent gas only.

Example 21

Production of 2-butoxyethanol in a Continuous Unit Using a Carbon Support

The reactor tube was loaded with 40 mL (17.1 g) of 1% Pd on carbon support CG5. This catalyst was used in all the following experiments unless indicated. The reactor was pressurized to 2.4 MPa with $H_2$ and heated to 200° C. PDX was fed to the reactor at 0.56 mL/min and EG was fed to the reactor at 2.11 mL/min. The molar ratio of EG:PDX was 8.4. $H_2$ was fed to the reactor at 600 SCCM which corresponded to an $H_2$:PDX molar ratio of 6. After 7.5 h online, 92% PDX conversion was achieved. Product selectivity was found to be as follows: EB 90.4%, 1,2-dibutoxyethane 8.7%, ethyl butyrate 0.64%, EG Monobutyrate 0.86%. The specific production rate of EB was 656 g EB/L·h. Thus, catalyst activity with a carbon support at 7.5 hrs was good.

Examples 22-27

Production of 2-butoxyethanol in a Continuous Unit

These examples were carried out using the apparatus described above with the conditions and results listed in the Table 5 below. Catalyst activity and selectivity with a carbon support at 7.5 hrs were good in many examples, especially those run with BASF 1% Pd on carbon support CG5 catalyst at high EG:PDX mole ratios.

TABLE 5

| Ex. | Temp (° C.) | Press (MPa) | Liquid Feed Rate mL/min | EG: PDX | $H_2$ Feed (SCCM) | PDX Conversion | % $EB^a$ | % 1,2-$DBE^b$ | % $EtOBu^c$ | % $EGB^d$ | % nBuOH | Production g EB/ L·h |
|---|---|---|---|---|---|---|---|---|---|---|---|---|
| 22 | 150 | 3.45 | 1.33 | 11 | 600 | 76.8% | 85.7% | 12.2% | 2.1% | 0% | 0% | 196 |
| 23† | 200 | 2.4 | 2.66 | 8.7 | 600 | 42.6% | 82.8% | 9.3% | 3.8% | 3.6% | 0% | 365 |
| 24‡ | 200 | 2.4 | 3.34 | 8.6 | 600 | 59.2% | 92.8% | 7.0% | 0.5% | 0.8% | 0% | 519 |
| 25 | 175 | 3.45 | 13.3 | 17 | 1000 | 47.3% | 93.3% | 5.3% | 0.3% | 0.4% | 0.8% | 904 |
| 26 | 200 | 3.45 | 13.3 | 15 | 1000 | 62.2% | 92.2% | 6.5% | 1.0% | 0.3% | 0.6% | 515 |
| 27 | 185 | 4.48 | 11.4 | 4.8 | 1000 | 1.5% | 78.9% | 14.9% | 4.4% | 0.2% | 0% | 41.7 |

†—Sud-Chemie NobleMax 111 (0.5% Pd/C)
‡—BASF 0.5% Pd/CG5
$^a$2-butoxyethanol
$^b$1,2-dibutoxyethane
$^c$ethyl butyrate
$^d$EG monobutyrate Example 28

Production of 2-butoxyethanol in a Long-Term Continuous Unit Using a Carbon Support Using the apparatus described above, 40 mL of 1% Pd/CG5 (BASF) was loaded into the reactor tube. The reactor was pressurized to 3.44 MPa with $H_2$ and heated to 175° C. PDX was fed to the reactor at 1.31 mL/min and EG was fed to the reactor at 9.20 mL/min. The molar ratio of EG:PDX was 10.2. $H_2$ is fed to the reactor at 1000 SCCM, which corresponded to an $H_2$:PDX molar ratio of 4.2. The reactor was maintained at temperature and pressure with continuous feed and take-off for 24 h/day for 3 weeks. After 50 h on-line, the average conversion was 50% and the average selectivity to EB was 92%. From 50 h on-line to 220 h on-line, the average conversion was 30% and the average selectivity was 95%. After 340 h on-line, the experiment was discontinued. The observed specific production rate of EB was 526 g EB/L·h. The conversion over the life of the catalyst up to 340 hrs was 34%, and the selectivity to EB over the life of the catalyst was 91.2%.

Examples 29-36

Production of 2-butoxyethanol in a Continuous Unit

These examples were carried out using the apparatus described above with the conditions and results listed in the Table 6 below. The reaction was carried out over a 2% Pd/SiO$_2$ catalyst from Evonik Degussa (Noblyst 1005). The catalyst was run in a similar long-term experiment. The lifetime of the catalyst during that run was 475 h with a conversion of 31% and a selectivity of 97%.

TABLE 6

| Ex. | Temp (° C.) | Press. (MPa) | Liquid Feed Rate (mL/min) | EG:PDX | H$_2$ Feed (SCCM) | PDX Conversion | % EB$^a$ | % 1,2-DBE$^b$ | % EtOBu$^c$ | % EGB$^d$ | % nBuOH | Production (lbs EB/ft$^3$·h) |
|---|---|---|---|---|---|---|---|---|---|---|---|---|
| 29 | 175 | 2.44 | 13.3 | 17 | 1000 | 14.6% | 97.8% | 1.0% | 0.6% | 0.02% | 0% | 254 |
| 30 | 175 | 3.45 | 13.3 | 17 | 1000 | 24.8% | 98.0% | 0.8% | 0.4% | 0.5% | 0% | 426 |
| 31 | 175 | 4.31 | 13.3 | 17 | 1000 | 35.1% | 96.0% | 2.9% | 0.3% | 0.6% | 0% | 596 |
| 32 | 175 | 5.17 | 13.3 | 17 | 1000 | 36.5% | 97.6% | 1.5% | 0.3% | 0.03% | 0.1% | 713 |
| 33 | 175 | 6.89 | 13.3 | 20 | 1000 | 42.8% | 98.1% | 0.9% | 0.2% | 0.1% | 0.2% | 713 |
| 34 | 175 | 5.17 | 13.3 | 7.1 | 1000 | 31.2% | 97.8% | 2.1% | 0.0% | 0.0% | 0.03% | 1319 |
| 35 | 175 | 3.45 | 13.3 | 9.6 | 1000 | 22.6% | 96.7% | 1.7% | 0.4% | 1.2% | 0.0% | 694 |
| 36 | 175 | 5.17 | 13.3 | 5.5 | 1000 | 42.9% | 94.5% | 4.8% | 0.4% | 0.3% | 0% | 1987 |

$^a$2-butoxyethanol
$^b$1,2-dibutoxyethane
$^c$ethyl butyrate
$^d$EG monobutyrate

The invention claimed is:

1. A process for making a hydroxy mono-ether compound, comprising:
   feeding a cyclic acetal or cyclic ketal compound and hydrogen, without feeding a carbonyl compound, into a reaction vessel;
   reacting the cyclic acetal or cyclic ketal compound with the hydrogen in the presence of (i) a noble metal catalyst supported on carbon or silica and (ii) a solvent comprising a polyhydroxyl compound used to make the cyclic acetal or cyclic ketal compound, to form a hydroxy mono-ether compound,
   wherein the reaction is carried out in the absence of an added acidic co-catalyst or promoter, and
   wherein the molar ratio of the polyhydroxyl compound to the cyclic acetal or cyclic ketal compound is at least 2:1.

2. The process according to claim 1, wherein the cyclic acetal or cyclic ketal compound has the structure of Formula I:

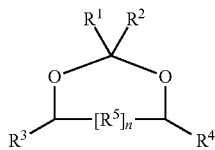

I wherein R$^1$, R$^2$, R$^3$, and R$^4$ are each independently H or a branched or un-branched C$_1$-C$_6$ alkyl group;

wherein no more than one of R$^1$ and R$^2$ is H;
wherein R$^5$ is a branched or un-branched divalent alkyl group having 1 to 6 carbon atoms; and
wherein n is 0 or 1.

3. The process according to claim 1, wherein the cyclic acetal or cyclic ketal compound comprises 2-propyl-1,3-dioxolane, 2-propyl-1,3-dioxane, 2-ethyl-1,3-dioxolane, 2-ethyl-1,3-dioxane, 2-methyl-1,3-dioxolane, 2-methyl-1,3-dioxane, 2-propyl-4-methyl-1,3-dioxane, 5,5-dimethyl-2-propyl-1,3-dioxane, 5,5-dimethyl-2-ethyl-1,3-dioxane, 2-ethyl-1,3-dioxepane, or 2-ethyl-1,3,6-trioxocane.

4. The process according to claim 1, wherein the polyhydroxyl compound comprises ethylene glycol, 1,2-propanediol, 1,3-propanediol, 1,4-butanediol, 1,3-butanediol, diethylene glycol, triethylene glycol, glycerin, trimethylolpropane, xylitol, arabitol, 1,2- or 1,3-cyclopentanediol, 1,2- or 1,3-cyclohexanediol, 2,3-norbornanediol, or combinations thereof.

5. The process according to claim 1, wherein the polyhydroxyl compound comprises ethylene glycol, 1,2-propanendiol, 1,3-propanediol, or combinations thereof.

6. The process according to claim 1, wherein the molar ratio of the polyhydroxyl compound to the cyclic acetal or cyclic ketal compound is from 3:1 to 20:1.

7. The process according to claim 1, wherein the molar ratio of the polyhydroxyl compound to the cyclic acetal or cyclic ketal compound is from 5:1 to 20:1.

8. The process according to claim 1, wherein the hydroxyl mono-ether compound comprises ethylene glycol monobutyl ether, 3-butoxy-1-propanol, ethylene glycol monopropyl ether, 3-propoxy-1-propanol, ethylene glycol monoethyl ether, 3-ethoxy-1-propanol, 3-butoxy-2,2-dimethyl-1-propanol, 4-propoxy-1-butanol, diethylene glycol monobutyl ether, or combinations thereof.

9. The process according to claim 1, which has a selectivity of at least 80% for the hydroxy mono-ether compound.

10. The process according to claim 1, which has a selectivity of at least 90% for the hydroxy mono-ether compound.

11. The process according to claim 1, which has a selectivity of at least 95% for the hydroxy mono-ether compound.

12. The process according to claim 11, wherein the conversion of the cyclic acetal or cylic ketal compound is from 85% to 98%.

13. The process according to claim 1, wherein the noble metal catalyst comprises palladium.

14. The process according to claim 1, wherein the reaction is carried out in the absence of hydroquinone.

15. A process for preparing a hydroxy mono-ether compound, comprising:

(a) reacting a carbonyl compound with a polyhydroxyl compound in the presence of an acid catalyst to form a cyclic acetal or cyclic ketal compound;

(b) feeding the cyclic acetal or cyclic ketal compound and hydrogen, without feeding the carbonyl compound, into a reaction vessel; and (c) reacting the cyclic acetal or cyclic ketal compound with the hydrogen in the presence of (i) a noble metal catalyst supported on carbon or silica and (ii) a solvent comprising the polyhydroxyl compound to form a hydroxy mono-ether compound, wherein the reaction in step (c) is carried out in the absence of an added acidic co-catalyst or promoter, and wherein the molar ratio of the polyhydroxyl compound to the cyclic acetal or cyclic ketal compound in step (c) is at least 2:1.

16. The process according to claim 15, wherein the carbonyl compound comprises an aldehyde compound selected from the group consisting of acetaldehyde, propionaldehyde, butyraldehyde, isobutyraldehyde, pentaldehyde, 2-methylbutyraldehyde, 3-methylbutyraldehyde, hexaldehyde, benzaldehyde, 2-ethylhexaldehyde, octanal, and nonanal.

17. The process according to claim 15, wherein the carbonyl compound comprises a ketone compound selected from the group consisting of acetone, methyl isobutyl ketone, methyl ethyl ketone, methyl propyl ketone, methyl isopropyl ketone, methyl isobutyl ketone, 2-hexanone, cyclohexanone, 2-heptanone, 4-heptanone, and 2-octonone.

18. The process according to claim 15, wherein the polyhydroxyl compound comprises ethylene glycol, 1,2-propanediol, 1,3-propanediol, 1,4-butanediol, 1,3-butanediol, diethylene glycol, triethylene glycol, glycerin, trimethylolpropane, xylitol, arabitol, 1,2- or 1,3-cyclopentanediol, 1,2- or 1,3-cyclohexanediol, 2,3-norbornanediol, or combinations thereof.

19. The process according to claim 15, wherein the polyhydroxyl compound comprises ethylene glycol, 1,2-propanediol, 1,3-propanediol, or combinations thereof.

20. The process according to claim 15, wherein the molar ratio of the polyhydroxyl compound to the cyclic acetal or cyclic ketal compound in step (c) is from 5:1 to 20:1.

21. The process according to claim 15, wherein the hydroxyl mono-ether compound comprises ethylene glycol monobutyl ether, 3-butoxy-1-propanol, ethylene glycol monopropyl ether, 3-propoxy-1-propanol, ethylene glycol monoethyl ether, 3-ethoxy-1-propanol, 3-butoxy-2,2-dimethyl-1-propanol, 4-propoxy-1-butanol, diethylene glycol monobutyl ether, or combinations thereof.

22. The process according to claim 15, which has a selectivity of at least 90% for the hydroxy mono-ether compound.

23. The process according to claim 15, which has a selectivity of at least 95% for the hydroxy mono-ether compound.

24. The process according to claim 23, wherein the conversion of the cyclic acetal or cylic ketal compound is from 85% to 98%.

25. The process according to claim 15, wherein the noble metal catalyst comprises palladium.

* * * * *